(12) United States Patent
Monclin

(10) Patent No.: US 9,221,734 B2
(45) Date of Patent: Dec. 29, 2015

(54) METHODS AND APPARATUS FOR REMOVING DISSOLVED GASES FROM FERMENTATION STREAMS

(71) Applicant: API Intellectual Property Holdings, LLC, Atlanta, GA (US)

(72) Inventor: Jean-Pierre Monclin, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 14/598,277

(22) Filed: Jan. 16, 2015

(65) Prior Publication Data

US 2015/0218070 A1     Aug. 6, 2015

Related U.S. Application Data

(60) Provisional application No. 61/934,409, filed on Jan. 31, 2014.

(51) Int. Cl.
  *C07C 29/76*    (2006.01)
  *B01D 19/00*    (2006.01)
  *G01N 31/22*    (2006.01)

(52) U.S. Cl.
  CPC ............ *C07C 29/76* (2013.01); *B01D 19/0036* (2013.01); *B01D 19/0078* (2013.01); *G01N 31/22* (2013.01)

(58) Field of Classification Search
  CPC ...................................................... G01N 31/22
  USPC ........................................................ 422/404
  See application file for complete search history.

(56) References Cited

U.S. PATENT DOCUMENTS 8,133,451 B2 *   3/2012   Yuan .............................. 422/404

* cited by examiner

*Primary Examiner* — Elvis O Price
(74) *Attorney, Agent, or Firm* — Ryan P. O'Connor

(57) ABSTRACT

The present invention provides a method of treating a fermentation stream to remove dissolved gases, comprising obtaining a fermentation stream including water, one or more fermentation products, and dissolved gases; continuously sonicating the fermentation stream to generate acoustically cavitated gases from the dissolved gases; and applying vacuum to release the acoustically cavitated gases from the fermentation stream. The dissolved gases may include air, oxygen, nitrogen, helium, argon, carbon dioxide, carbon monoxide, hydrogen, or other non-condensables. The release of acoustically cavitated gases may optionally be done simultaneously with sonication. At least 75%, such as up to 95% or more, of the dissolved gases may be released from the fermentation stream. The disclosed method positively impacts downstream operations and product quality by removing dissolved gases.

19 Claims, 1 Drawing Sheet

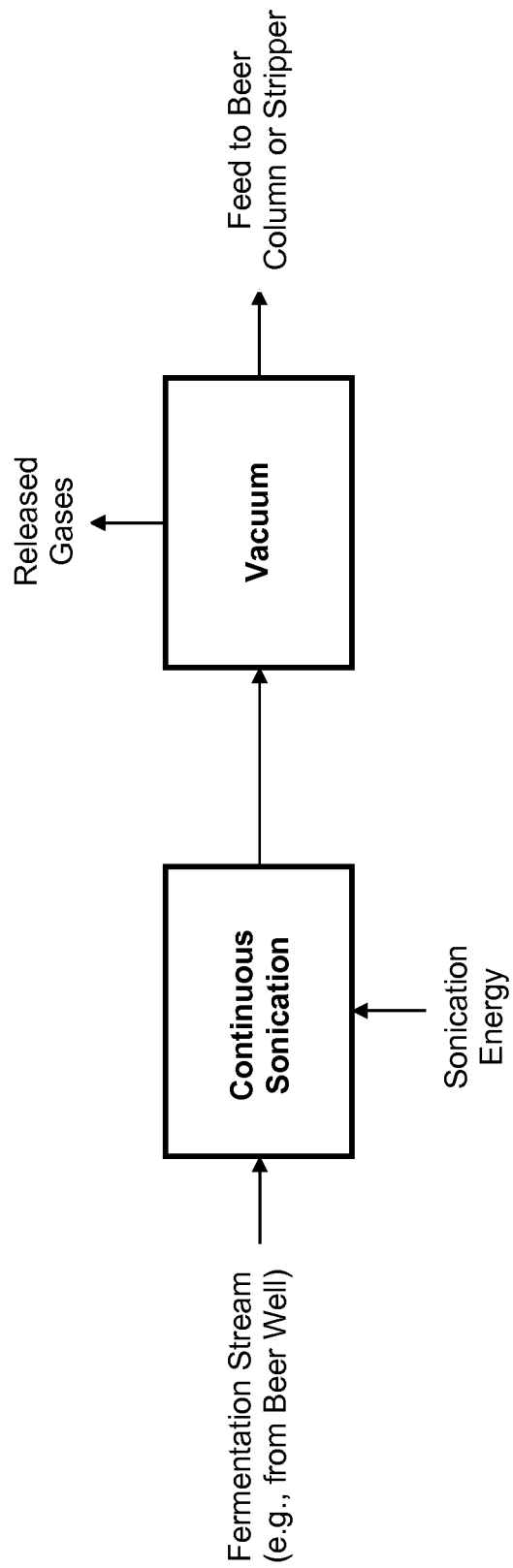

METHODS AND APPARATUS FOR REMOVING DISSOLVED GASES FROM FERMENTATION STREAMS

PRIORITY DATA

This patent application is a non-provisional application claiming priority to U.S. Provisional Patent App. No. 61/934,409, filed Jan. 31, 2014, which is hereby incorporated by reference herein.

FIELD

The present invention generally relates to treatment of fermentation streams in biorefineries to remove dissolved gases, such as carbon dioxide.

BACKGROUND

Many biorefinery fermentation processes will generate carbon dioxide as a co-product of fermentation. The carbon dioxide will ultimately need to be removed from the process, as it should not be contained in the final product stream. Typically, carbon dioxide and other dissolved gases simply remain in fermentation broths until removed in a stripper or distillation column.

However, several negative effects result from conventional processing in this manner. First, the presence of large quantities of carbon dioxide reduces the capacity of the beer column or stripper. Second, large concentrations of carbon dioxide cause the formation of carbonic acid, thereby reducing pH which increases the potential for corrosion and other equipment concerns.

What is desired is an economical method to remove carbon dioxide and other dissolved gases from fermentation streams, while preserving yields of desired products (such as ethanol).

SUMMARY

The present invention addresses the aforementioned needs in the art.

In some variations, the disclosure provides a method of treating a fermentation stream to remove dissolved gases, the method comprising:
(a) obtaining a fermentation stream comprising water, one or more fermentation products, and dissolved gases;
(b) continuously or semi-continuously sonicating the fermentation stream, to generate, in the fermentation stream, acoustically cavitated gases comprising at least a portion of the dissolved gases; and
(c) releasing at least a portion of the acoustically cavitated gases from the fermentation stream, thereby forming a treated fermentation stream.

In some embodiments, the method (i.e., all steps) is continuous or semi-continuous. The method may also be conducted as a batch process, including step (b) (i.e., batch sonication may be employed).

In some embodiments, the one or more fermentation products comprise ethanol. The principles of the invention are not limited to any particular fermentation product. The only requirement is that the fermentation stream obtained from a fermentor or a downstream unit contain one or more dissolved gases, such as (but not limited to) carbon dioxide.

In various embodiments, the dissolved gases include one or more gases selected from the group consisting of air, oxygen, nitrogen, helium, argon, carbon dioxide, carbon monoxide, hydrogen, ozone, sulfur oxides, nitrogen oxides, ammonia, methane, and hydrogen chloride. In certain embodiments, such as relating to ethanol production, the dissolved gases include carbon dioxide or consist essentially of carbon dioxide. Of course, small amounts of air and other trace gases will typically be present in any industrial liquid stream.

In some exemplary embodiments, step (b) utilizes a sonication frequency in the range of about 1 kHz to about 1000 kHz, such as about 10 kHz to about 500 kHz, or about 20 kHz to about 100 kHz.

In some exemplary embodiments, step (b) utilizes a sonication time in the range of about 1 minute to about 24 hours, such as about 5 minutes to about 4 hours, or about 10 minutes to about 1 hour.

The releasing in step (c) may be conducted with a reduction in pressure. For example, the method may include comprising applying vacuum to the fermentation stream. When vacuum is employed, step (c) may include a vacuum pressure in the range of about 0.01 bar to about 0.99 bar absolute pressure, such as 0.1 bar to about 0.95 bar, or about 0.5 bar to about 0.9 bar.

Alternatively, or additionally, the releasing in step (c) may include a vapor disengagement of the acoustically cavitated gases. In some of these embodiments, the vapor disengagement utilizes a sweep gas.

In some embodiments, steps (b) and (c) are conducted simultaneously. That is, the release of acoustically cavitated gases may be done simultaneously with sonication. Steps (b) and (c) may be conducted sequentially, such as alternating between sonication and release of acoustically cavitated gases (which may be repeated in number of times). In certain embodiments, the step of sonication is completed and then, in a separate unit, the acoustically cavitated gases are released by vacuum or other means.

In some embodiments, at least 75%, 85%, or 95% of the dissolved gases are released from the fermentation stream. In some embodiments, at least 80%, 90%, or 98% of the dissolved gases are acoustically cavitated. In some embodiments, at least 85%, 95%, or 99% of the acoustically cavitated gases are released. These fractions are exemplary only, and other embodiments may be desirable wherein a lower fraction (e.g., about half) of dissolved gases is acoustically cavitated and/or a lower fraction (e.g., about three-fourths) of acoustically cavitated gases is released. Also, when more than one dissolved gas is present, the fraction of each gas that is acoustically cavitated, along with the fraction of each acoustically cavitated gas that is ultimately released, may vary according to compound type or concentration.

In some variations, the fermentation stream is obtained from fermenting sugars derived by fractionating lignocellulosic biomass in the presence of water, a solvent for lignin, and an acid or acid precursor to form cellulose, hemicellulose, and lignin, followed by hydrolysis of the cellulose and/or the hemicellulose to generate the sugars.

In some variations, the fermentation stream is obtained from fermenting sugars derived by extracting hemicelluloses from lignocellulosic biomass in the presence of steam or hot water, followed by hydrolysis of the hemicellulose to generate the sugars.

In any of these embodiments, the overall method may further include introducing the treated fermentation stream to a distillation or stripping column, to concentrate the one or more fermentation products in the treated fermentation stream. In certain embodiments, the release of acoustically cavitated gas is integrated, at least to some extent, with distillation or stripping.

In some particular embodiments, the disclosure provides a continuous method of treating a fermentation stream to remove carbon dioxide, the method comprising:

(a) obtaining a fermentation stream comprising water, one or more fermentation products, and dissolved carbon dioxide;

(b) sonicating the fermentation stream at a sonication frequency in the range of about 20 kHz to about 100 kHz and a sonication time in the range of about 10 minutes to about 1 hour, to generate acoustically cavitated carbon dioxide comprising at least a portion of the dissolved carbon dioxide; and (c) releasing at least a portion of the acoustically cavitated carbon dioxide from the fermentation stream by applying vacuum to a pressure in the range of about 0.5 bar to about 0.9 bar absolute pressure, thereby forming a treated fermentation stream.

In some particular embodiments, the disclosure provides a system for treating a fermentation stream to remove carbon dioxide, the system comprising:

a sonication unit in communication with a fermentation stream comprising water, one or more fermentation products, and dissolved carbon dioxide, wherein the sonication unit is capable of sonicating the fermentation stream at a sonication frequency in the range of about 1 kHz to about 1000 kHz and a sonication time in the range of about 1 minute to about 24 hours, to generate acoustically cavitated carbon dioxide comprising at least a portion of the dissolved carbon dioxide; and a separation unit capable of releasing, under vacuum, at least a portion of the acoustically cavitated carbon dioxide at a pressure in the range of about 0.01 bar to about 0.99 bar absolute pressure.

In some variations, the disclosure provides a system for removing dissolved gases from a fermentation stream, the system comprising:

a sonication unit configured for continuously or semi-continuously sonicating a fermentation stream comprising water and dissolved gases, to generate acoustically cavitated gases comprising at least a portion of the dissolved gases; and a separation unit, in operable communication with the sonication unit, configured for releasing at least a portion of the acoustically cavitated gases from the fermentation stream.

BRIEF DESCRIPTION OF THE DRAWING

FIG. 1 is a block-flow diagram depicting some variations of the invention for treating a fermentation stream to remove dissolved gases by sonication.

DETAILED DESCRIPTION OF SOME EMBODIMENTS

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. For example, reference to "unit" also includes a plurality of units (e.g., reactors or vessels). Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

The present invention addresses the problem of carbon dioxide or other dissolved gases contained in fermentation streams, and the negative impacts on processing such streams for recovery of fermentation products. Some variations are premised in the realization that sonication may be configured to control the removal of various gases from fermentation broths before introducing the broths (e.g., beer stream) into a stripper or distillation column. In particular, sonication followed by vacuum will de-gas and remove the majority of dissolved, non-condensable gases ($CO_2$, air, nitrogen, etc.) contained in the fermentation broth.

Various benefits can be potentially realized in some embodiments of the invention. For example, removing $CO_2$ (and/or other non-condensable gases) may positively impact the operation of the beer column or stripper. Also, removing $CO_2$ (and/or other gases) may allow production of ethanol (or other product) at a higher pH (such as 6 or higher), due to reduced formation potential for carbonic acid or other acids derived from other gases. Finally, removing non-condensable gases may increase the capacity of condenser(s) connected to the beer column or stripper. FIG. 1 is a block-flow diagram depicting some variations of the invention for treating a fermentation stream to remove dissolved gases by sonication.

For purposes of this disclosure, "sonication" means application of sound energy typically in the frequency range of 1 kHz to 1000 kHz. For purposes of this disclosure, "acoustic cavitation" means the formation, growth, and implosive collapse of bubbles in a liquid.

In some variations, the disclosure provides a method of treating a fermentation stream to remove dissolved gases, the method comprising:

(a) obtaining a fermentation stream comprising water, one or more fermentation products, and dissolved gases;

(b) continuously or semi-continuously sonicating the fermentation stream, to generate, in the fermentation stream, acoustically cavitated gases comprising at least a portion of the dissolved gases; and (c) releasing at least a portion of the acoustically cavitated gases from the fermentation stream, thereby forming a treated fermentation stream.

In some embodiments, the method (i.e., some or all steps) is continuous or semi-continuous. The method may also be conducted as a batch process, including step (b)—i.e., batch sonication may be employed.

In some embodiments, the one or more fermentation products comprise ethanol. The principles of the invention are not limited to any particular fermentation product. The only requirement is that the fermentation stream obtained from a fermentor or a downstream unit contain one or more dissolved (soluble), suspended (insoluble), or entrained gases, such as (but not limited to) carbon dioxide.

In various embodiments, the dissolved gases include one or more gases selected from the group consisting of air, oxygen, nitrogen, helium, argon, carbon dioxide, carbon monoxide, hydrogen, ozone, sulfur oxides, nitrogen oxides, ammonia, methane, and hydrogen chloride. In certain embodiments, such as relating to ethanol production, the dissolved gases include carbon dioxide or consist essentially of carbon dioxide. Of course, small amounts of air and other trace gases will typically be present in any industrial liquid stream.

In some exemplary embodiments, step (b) utilizes a sonication frequency in the range of about 1 kHz to about 1000 kHz, such as about 10 kHz to about 500 kHz, or about 20 kHz to about 100 kHz. In certain embodiments, the sonication frequency is greater than 20 kHz, which is generally known as ultrasonication. In various embodiments, step (b) utilizes a sonication frequency of about 5, 10, 15, 20, 25, 30, 35, 40, 45, 50, 60, 70, 80, 90, 100, 150, 200, 250, 300, 400, 500, 600, 700, 800, or 900 kHz, for example.

In some exemplary embodiments, step (b) utilizes a sonication time in the range of about 1 minute to about 24 hours, such as about 5 minutes to about 4 hours, or about 10 minutes to about 1 hour. In various embodiments, step (b) utilizes a sonication time of about 5, 10, 15, 20, 30, 45, 60, 75, or 90 minutes, or about 1, 2, 3, 4, 6, 8, 10, 12, 18 hours.

The releasing in step (c) may be conducted with a reduction in pressure. For example, the method may include applying vacuum to the fermentation stream. When vacuum is employed, step (c) may include a vacuum pressure in the range of about 0.01 bar to about 0.99 bar absolute pressure, such as 0.1 bar to about 0.95 bar, or about 0.5 bar to about 0.9 bar.

Alternatively, or additionally, the releasing in step (c) may include a vapor disengagement of the acoustically cavitated gases. In some of these embodiments, the vapor disengagement utilizes a sweep gas. The sweep gas may be the same gas as one of the acoustically cavitated gases, or the sweep gas may be different. For example, the sweep gas may be air to remove acoustically cavitated $CO_2$. Or the sweep gas may be compressed $CO_2$ (for example) to remove acoustically cavitated $CO_2$. The sweep gas may be introduced at high velocities to ensure the acoustically cavitated gas does not re-dissolve into the liquid or to minimize the sweep gas itself dissolving into the liquid.

In some embodiments, steps (b) and (c) are conducted simultaneously. That is, the release of acoustically cavitated gases may be done simultaneously with sonication. Steps (b) and (c) may be conducted sequentially, such as alternating between sonication and release of acoustically cavitated gases (which may be repeated any number of times, such as 1, 2, 3, 4, or more times). In certain embodiments, the step of sonication is completed and then, in a separate unit, the acoustically cavitated gases are released by vacuum or other means.

In some embodiments, at least 50%, 55%, 60%, 65%, 70%, 75%, 80%, 85%, 90%, 91%, 92%, 93%, 94%, 95% or more of the dissolved gases are released from the fermentation stream. In order for the dissolved gases to be released according to the methods disclosed herein, acoustically cavitated gases are released by some means, such as vacuum. The overall fraction of dissolved gases released from the fermentation stream therefore depends on the fraction that is actually cavitated as well as the fraction of the cavitated gases that are then released. For example, if 90% of the initial dissolved gases are acoustically cavitated and 90% of the resulting acoustically cavitated gases are then released, the yield of initial dissolved gases released is 81% (neglecting any non-cavitated gases that may be released directly from solution by application of vacuum, according to solution equilibrium).

In some embodiments, at least 50%, 55%, 60%, 65%, 70%, 75%, 80%, 85%, 90%, 91%, 92%, 93%, 94%, 95% or more of the dissolved gases are acoustically cavitated. This fraction may vary with the severity of sonication (e.g., frequency or time), and there may be an economic optimum in view of sonication cost. Also the fraction will be expected to depend on the particular gases present, since different gases will have different cavitation potential and different fluid-dynamic properties when cavitated. It will be recognized that some fraction of acoustically cavitated gases may re-dissolve into the liquid, depending for example on the time between sonication and release, the type of gas, the conditions present in the liquid, temperature, pressure, pH, etc.

In some embodiments, at least 50%, 55%, 60%, 65%, 70%, 75%, 80%, 85%, 90%, 91%, 92%, 93%, 94%, 95%, 96%, 97%, 98%, 99% or more of the acoustically cavitated gases are released. This fraction may vary with the means of release, such as the amount of vacuum applied, the quantity of sweep gas, and so on. Also the fraction will be expected to depend on the particular gases present, due to varying vapor pressures, diffusivities, etc.

These fractions are exemplary only, and other embodiments may be desirable wherein a lower fraction (e.g., about half) of dissolved gases is acoustically cavitated and/or a lower fraction (e.g., about three-fourths) of acoustically cavitated gases is released. Also, when more than one dissolved gas is present, the fraction of each gas that is acoustically cavitated, along with the fraction of each acoustically cavitated gas that is ultimately released, may vary as a function of compound type or concentration.

In some embodiments, the removal of dissolved $CO_2$ is controlled to adjust the pH of a beer stream by reducing the presence of carbonic acid in the stream. For example, the beer stream pH may be adjusted to a pH of about 5 to about 8, such as about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. The pH of other liquid streams in the process may be controlled in a similar manner.

In some variations, the fermentation stream is obtained from fermenting sugars derived by fractionating lignocellulosic biomass in the presence of water, a solvent for lignin, and an acid or acid precursor to form cellulose, hemicellulose, and lignin, followed by hydrolysis of the cellulose and/or the hemicellulose to generate the sugars. Some of these variations are related to the commonly assigned AVAP® technology.

In some variations, the fermentation stream is obtained from fermenting sugars derived by extracting hemicelluloses from lignocellulosic biomass in the presence of steam or hot water, followed by hydrolysis of the hemicellulose to generate the sugars. Some of these variations are related to the commonly assigned Green Power+® technology.

In any of these embodiments, the overall method may further include introducing the treated fermentation stream to a distillation or stripping column, to concentrate one or more fermentation products in the treated fermentation stream. Removal of dissolved, non-condensable gases is expected to improve operations of the distillation or stripping column, such as increased capacity, reduced maintenance requirements, or other benefits.

In certain embodiments, the release of acoustically cavitated gas is integrated, at least to some extent, with distillation or stripping. For example, a distillation or stripping column may be designed to additionally remove the released, acoustically cavitated gases in one or more locations. In certain of these embodiments, a portion of the acoustically cavitated gases may function as a stripping vapor in a region of the column, followed by disengagement of the acoustically cavitated gases from the rest of the solution or vapor (e.g., ethanol/water).

In some particular embodiments, a continuous method of treating a fermentation stream to remove carbon dioxide comprises:
(a) obtaining a fermentation stream comprising water, one or more fermentation products, and dissolved carbon dioxide;
(b) sonicating the fermentation stream at a sonication frequency in the range of about 20 kHz to about 100 kHz and a sonication time in the range of about 10 minutes to about 1 hour, to generate acoustically cavitated carbon dioxide comprising at least a portion of the dissolved carbon dioxide; and
(c) releasing at least a portion of the acoustically cavitated carbon dioxide from the fermentation stream by applying vacuum to a pressure in the range of about 0.5 bar to about 0.9 bar absolute pressure, thereby forming a treated fermentation stream.

In some particular embodiments, a system for treating a fermentation stream to remove carbon dioxide comprises:
a sonication unit in communication with a fermentation stream comprising water, one or more fermentation products, and dissolved carbon dioxide, wherein the sonication unit is capable of sonicating the fermentation stream at a sonication frequency in the range of about 1 kHz to about 1000 kHz and a sonication time in the range of about 1 minute to about 24 hours, to generate acoustically cavitated carbon dioxide comprising at least a portion of the dissolved carbon dioxide; and
a separation unit capable of releasing, under vacuum, at least a portion of the acoustically cavitated carbon dioxide at a pressure in the range of about 0.01 bar to about 0.99 bar absolute pressure.

The biomass feedstock may be selected from hardwoods, softwoods, forest residues, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.).

Various moisture levels may be associated with the starting biomass. The biomass feedstock need not be, but may be, relatively dry. In general, the biomass is in the form of a particulate or chip, but particle size is not critical in this invention.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, 1,4-butanediol, 2,3-butanediol, lactic acid, succinic acid, or any other fermentation products. Some amount of the fermentation product may be a microorganism or enzymes, which may be recovered if desired.

When the fermentation will employ bacteria, such as *Clostridia* bacteria, it is preferable to further process and condition the hydrolysate to raise pH and remove residual $SO_2$ and other fermentation inhibitors. Sonication using the methods described herein may be employed to acoustically cavitate residual SO2, followed by stripping and/or vacuum release. Alternatively, or additionally, residual $SO_2$ may be catalytically oxidized to convert residual sulfite ions to sulfate ions by oxidation. This oxidation may be accomplished by adding an oxidation catalyst, such as $FeSO_4.7H_2O$, that oxidizes sulfite ions to sulfate ions. Preferably, the residual $SO_2$ is reduced to less than about 100 ppm, 50 ppm, 25 ppm, 10 ppm, 5 ppm, or 1 ppm.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step when a solvent is utilized. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives.

The present invention also provides systems configured for carrying out the disclosed processes, and compositions produced therefrom. Any stream generated by the disclosed processes may be partially or completed recovered, purified or further treated, and/or marketed or sold.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method of treating a fermentation stream to remove dissolved gases, said method comprising:
    (a) obtaining a fermentation stream comprising water, one or more fermentation products, and dissolved gases;
    (b) continuously or semi-continuously sonicating said fermentation stream to generate, in said fermentation stream, acoustically cavitated gases comprising at least a portion of said dissolved gases; and
    (c) releasing at least a portion of said acoustically cavitated gases from said fermentation stream, thereby forming a treated fermentation stream.

2. The method of claim 1, wherein said method is continuous or semi-continuous.

3. The method of claim 1, wherein said one or more fermentation products comprise ethanol.

4. The method of claim 1, wherein said dissolved gases include one or more gases selected from the group consisting of air, oxygen, nitrogen, helium, argon, carbon dioxide, carbon monoxide, hydrogen, ozone, sulfur oxides, nitrogen oxides, ammonia, methane, and hydrogen chloride.

5. The method of claim 4, wherein said dissolved gases include carbon dioxide.

6. The method of claim 1, wherein step (b) utilizes a sonication frequency in the range of about 1 kHz to about 1000 kHz.

7. The method of claim 1, wherein step (b) utilizes a sonication time in the range of about 1 minute to about 24 hours.

8. The method of claim 1, wherein said releasing in step (c) is conducted with a reduction in pressure.

9. The method of claim 8, said method comprising applying vacuum to said fermentation stream, wherein step (c) includes a vacuum pressure in the range of about 0.01 bar to about 0.99 bar absolute pressure.

10. The method of claim 1, wherein said releasing in step (c) includes a vapor disengagement of said acoustically cavitated gases.

11. The method of claim 10, wherein said vapor disengagement utilizes a sweep gas.

12. The method of claim 1, wherein steps (b) and (c) are conducted simultaneously.

13. The method of claim 1, wherein steps (b) and (c) are conducted sequentially.

14. The method of claim 1, wherein at least 75% of said dissolved gases are released from said fermentation stream.

15. The method of claim 14, wherein at least 85% of said dissolved gases are released from said fermentation stream.

16. The method of claim 1, wherein said fermentation stream is obtained from fermenting sugars derived by fractionating lignocellulosic biomass in the presence of water, a solvent for lignin, and an acid or acid precursor to form cellulose, hemicellulose, and lignin, followed by hydrolysis of said cellulose and/or said hemicellulose to generate said sugars.

17. The method of claim 1, wherein said fermentation stream is obtained from fermenting sugars derived by extracting hemicelluloses from lignocellulosic biomass in the presence of steam or hot water, followed by hydrolysis of said hemicellulose to generate said sugars.

18. The method claim 1, said method further comprising introducing said treated fermentation stream to a distillation or stripping column, to concentrate said one or more fermentation products in said treated fermentation stream.

19. A continuous method of treating a fermentation stream to remove carbon dioxide, said method comprising:
    (a) obtaining a fermentation stream comprising water, one or more fermentation products, and dissolved carbon dioxide;
    (b) sonicating said fermentation stream at a sonication frequency in the range of about 20 kHz to about 100 kHz and a sonication time in the range of about 10 minutes to about 1 hour, to generate acoustically cavitated carbon dioxide comprising at least a portion of said dissolved carbon dioxide; and
    (c) releasing at least a portion of said acoustically cavitated carbon dioxide from said fermentation stream by applying vacuum to a pressure in the range of about 0.5 bar to about 0.9 bar absolute pressure, thereby forming a treated fermentation stream.

* * * * *